(12) United States Patent
Brooks et al.

(10) Patent No.: US 9,226,965 B2
(45) Date of Patent: Jan. 5, 2016

(54) METHOD AND COMPOSITION FOR TREATING HEART FAILURE

(75) Inventors: Wesley W. Brooks, Dedham, MA (US); Oscar H.L. Bing, Winchester, MA (US)

(73) Assignee: U.S. DEPARTMENT OF VETERANS AFFAIRS, Washington, DC (US)

( * ) Notice: Subject to any disclaimer, the term of this patent is extended or adjusted under 35 U.S.C. 154(b) by 972 days.

(21) Appl. No.: 12/285,380

(22) Filed: Oct. 3, 2008

(65) Prior Publication Data

US 2009/0093535 A1    Apr. 9, 2009

Related U.S. Application Data

(60) Provisional application No. 60/960,598, filed on Oct. 5, 2007.

(51) Int. Cl.
*A61K 31/40* (2006.01)
*A61K 31/235* (2006.01)
*A61K 45/06* (2006.01)
*A61K 31/216* (2006.01)

(52) U.S. Cl.
CPC .............. *A61K 45/06* (2013.01); *A61K 31/216* (2013.01); *A61K 31/40* (2013.01)

(58) Field of Classification Search
USPC .................................................. 514/423, 532
See application file for complete search history.

(56) References Cited

U.S. PATENT DOCUMENTS 6,706,686 B2    3/2004    Long et al.
2003/0144340 A1    7/2003    Long et al.
2006/0025333 A1    2/2006    Long et al.

FOREIGN PATENT DOCUMENTS

WO    WO03/077909    * 9/2003

OTHER PUBLICATIONS

Baylin SB, DNA methylation and gene silencing in cancer. Nature Clinical Practice Oncology (2005) 2, S4-11.
Maestri NE, Brusilow SW, Clissold DB. et al., Long-term Treatment of Girls with Ornithine Transcarbamylase Deficiency. N Engl J Med 1996; 335:855-859.
Samid D, Shack S, Myers CE. Selective Growth Arrest and Phenotypic Reversion of Prostate Cancer Cells in Vitro by Nontoxic Pharmacological Concentrations of Phenylacetate. J Clinincal Investigation, Inc. 1993; 91:2288-2295 (May 1993).
Kang H-L, Benzer S, Min K-T, Life extension in *Drosophila* by feeding a drug . Proc Natl Acad Sci USA Jan. 22, 2002; vol. 99, No. 2:838-843.
Rishikof DC, Ricupero DA, Liu H, Goldstein RH. Phenylbutyrate Decreases Type I Collagen Production in Human Lung Fibroblasts. J Cell Biochem 91:740-748 (2004).
Gardian G, Browne SE. Choi D-K, et al., Neuroprotective Effects of Phenylbutyrate in the N171-82Q Transgenic Mouse Model of Huntington's Disease. J Biol Chem. 280, No. 1: 556-563 (Jan. 7, 2005).

(Continued)

*Primary Examiner* — San-Ming Hui
(74) *Attorney, Agent, or Firm* — Dinesh Agarwal, P.C.

(57) ABSTRACT

A method and composition for treating, preventing or ameliorating heart failure, cardiac hypertrophy, and/or myocardial dysfunction includes administering a therapeutically effective amount of a HDAC inhibitor, such as phenylbutyrate, in combination with an ACE inhibitor, such as captopril.

17 Claims, 13 Drawing Sheets

(56) References Cited

OTHER PUBLICATIONS

Brooks WW, Conrad CH, Marsilio E, Robinson KG, Bing OHL. Treatment Reverses Myocardial Dysfunction and Genotypic Changes Associated with Heart Failure. J Cardiac Failure 2006;12:S12. (Abstract #039—Aug. 2006).

Brooks WW, Conrad CH, Marsilio E, Robinson KG, Bing OHL. Reversal of Myocardial Dysfunction and Gene Expression Changes in the Failing Heart with Histone Deacetylase and Angiotensin Converting Enzyme Inhibitors. (Abstract submitted to American Heart Association for Circulation on May 30, 2007).

Brooks WW, Bing OHL, Robinson KG, Slawsky MT, Chaletsky DM, Conrad CH, Effect of Angiotensin-Converting Enzyme Inhibition on Myocardial Fibrosis and Function in Hypertrophied and Failing Myocardium from the Spontaneously Hypertensive Rat. Journal of the American Heart Association, Circulation 1997;96: 4002-4010.

Brooks WW, Bing OHL, Conrad CH, O'Neil L, Crow MT, Lakatta EG, Dostal DE, Baker KM, Boluyt MO, Captopril Modifies Gene Expression in Hypertrophied and Failing Hearts of Aged Spontaneously Hypertensive Rats. Hypertension 1997;30:1362-1368.

Jin H, Yang R, Awad TA, Wang F, Li W, Williams SP, Ogasawara A, Shimada B, Williams M, Feo G, Paoni NF, Effects of Early Angiotensin Converting Enzyme Inhibition on Cardiac Gene Expression After Acute Myocardial Infarction. Journal of the American Heart Association, Circulation 2001; 103:736-742).

Brooks WW, Conrad CH, Robinson KG, Bing OHL Synergistic Cardiotherapeutic Effect of Phenylbutyrate with Captopril or Losartan in the Treatment of Heart Failure. American Heart Association AHA, Clinical Science, Supp 2 Circulation, vol. 118, No. 18 (Abstract #4834—Oct. 28, 2008).

PCT International Search Report and the Written Opinion in International App. No. PCT/US08/11495, dated Feb. 5, 2009 (7 pp.).

Daosukho et al. Phenylbutyrate, a histone deacetylase inhibitor, protects against Adriamycin-induced cardiac injury, Online: Mar. 12, 2007, Free Radical Biology & Medicine, vol. 42, pp. 1818-1825 (2007).

Kasumov et al. New Secondary Metabolites of Phenylbutyrate in Humans and Rats, Drug Metabolism and Disposition, vol. 32, pp. 10-19 (2004).

Brooks WW, Conrad CH, Tran L, Robinson KG, Humphries DE, Bing OHL: Restoration of Myocardial Function in the Failing Heart. Presented at the seventh annual meeting of the Heart Failure Society of America in Los Vagas, Nevada on Sep. 21-24, 2003. Published in the proceedings of the seventh annual meeting of the Heart Failure Society of America. J Cardiac Failure 9 (suppl 5); 8, 2003 (Abstract # 22).

Brooks WW, Conrad CH, Robinson KG, Bing OHL. Synergistic Cardiotherapeutic Effect of Phenylbutyrate with Captopril or Losartan in the Treatment of Heart Failure. Circulation Nov. 2008;118; Suppl(2):946 (2 pages). Presented at the annual scientific session of the American Heart Association, in New Orleans, LA, 2008.

Bing OH, Brooks WW, Robinson KG, Slawsky MT, Hayes JA, Litwin SE, et al. The Spontaneously Hypertensive Rat as a Model of the Transition from Compensated Left Ventricular Hypertrophy to Failure. J Mol Cell Cardiol. Jan. 1995; 27(1): 383-96.

Conrad CH, Brooks WW, Hayes JA, Sen S, Robinson KG, Bing OH. Myocardial Fibrosis and Stiffness With Hypertrophy and Heart Failure in the Spontaneously Hypertensive Rat. Circulation. Jan. 1, 1995; 91(1): 161-70 (28 pages).

Giles TD. Renin-angiotensin system modulation for treatment and prevention of cardiovascular diseases: toward an optimal therapeutic strategy. Rev Cardiovasc Med. 2007; 8 Suppl 2: S14-21 (1 page).

Pfeffer JM, Pfeffer MA, Mirsky I, Braunwald E. Regression of left ventricular hypertrophy and prevention of left ventricular dysfunction by captopril in the spontaneously hypertensive rat. Proc Natl Acad Sci U S A May 1982;79(10):3310-4.

Hwang JJ, Allen PD, Tseng GC, Lam CW, Fananapazir L, Dzau VJ, et al. Microarray gene expression profiles in dilated and hypertrophic cardiomyopathic end-stage heart failure. Physiol Genomics Jul. 12, 2002;10(1):31-44.

Steenman M, Chen YW, Le Cunff M, Lamirault G, Varro A, Hoffman E, et al. Transcriptomal analysis of failing and nonfailing human hearts. Physiol Genomics Jan. 15, 2003;12(2):97-112.

Sihag S, Cresci S, Li AY, Sucharov CC, Lehman JJ. PGC-1alpha and ERRalpha target gene downregulation is a signature of the failing human heart. J Mol Cell Cardiol Feb. 2009;46(2):201-12.

Wellner M, Dechend R, Park JK, Shagdarsuren E, Al-Saadi N, Kirsch T, et al. Cardiac gene expression profile in rats with terminal heart failure and cachexia. Physiol Genomics Feb. 10, 2005;20(3):256-67.

Ueno S, Ohki R, Hashimoto T, Takizawa T, Takeuchi K, Yamashita Y, et al. DNA microarray analysis of in vivo progression mechanism of heart failure. Biochem Biophys Res Commun Aug. 8, 2003;307(4):771-7.

Kong SW, Bodyak N, Yue P, Liu Z, Brown J, Izumo S, et al. Genetic expression profiles during physiological and pathological cardiac hypertrophy and heart failure in rats. Physiol Genomics Mar. 21, 2005;21(1):34-42.

Schiekofer S, Shiojima I, Sato K, Galasso G, Oshima Y, Walsh K. Microarray analysis of Akt1 activation in transgenic mouse hearts reveals transcript expression profiles associated with compensatory hypertrophy and failure. Physiol Genomics Oct. 11, 2006;27(2):156-70.

Sakata Y, Chancey AL, Divakaran VG, Sekiguchi K, Sivasubramanian N, Mann DL. Transforming growth factor-beta receptor antagonism attenuates myocardial fibrosis in mice with cardiac-restricted overexpression of tumor necrosis factor. Basic Res Cardiol Jan. 2008;103(1):60-8.

Gao Z, Xu H, DiSilvestre D, Halperin VL, Tunin R, Tian Y, et al. Transcriptomic profiling of the canine tachycardia-induced heart failure model: global comparison to human and murine heart failure. J Mol Cell Cardiol Jan. 2006;40(1):76-86.

Sharma UC, Pokharel S, Evelo CT, Maessen JG. A systematic review of large scale and heterogeneous gene array data in heart failure. J Mol Cell Cardiol Mar. 2005;38 (3):425-32.

Gamier A, Fortin D, Delomenie C, Momken I, Veksler V, Ventura-Clapier R. Depressed mitochondrial transcription factors and oxidative capacity in rat failing cardiac and skeletal muscles. J Physiol Sep. 1, 2003;551(Pt 2):491-501.

Lei B, Lionetti V, Young ME, Chandler MP, d'Agostino C, Kang E, et al. Paradoxical downregulation of the glucose oxidation pathway despite enhanced flux in severe heart failure. J Mol Cell Cardiol Apr. 2004;36(4):567-76.

Strom CC, Aplin M, Ploug T, Christoffersen TE, Langfort J, Viese M, et al. Expression profiling reveals differences in metabolic gene expression between exerciseinduced cardiac effects and maladaptive cardiac hypertrophy. FEBS J Jun. 2005;272 (11):2684-95.

Stanley WC, Recchia FA, Lopaschuk GD. Myocardial substrate metabolism in the normal and failing heart. Physiol Rev Jul. 2005;85(3):1093-129.

Ingwall JS. Energy metabolism in heart failure and remodelling. Cardiovasc Res Feb. 15, 2009;81(3):412-9.

Taegtmeyer H. Cardiac metabolism as a target for the treatment of heart failure. Circulation Aug. 24, 2004;110(8):894-6.

Lewandowski ED, Kudej RK, White LT, O'Donnell JM, Vatner SF. Mitochondrial preference for short chain fatty acid oxidation during coronary artery constriction. Circulation Jan. 22, 2002;105(3):367-72.

Huss JM, Kelly DP. Mitochondrial energy metabolism in heart failure: a question of balance. J Clin Invest Mar. 2005;115(3):547-55.

Young ME, McNulty P, Taegtmeyer H. Adaptation and maladaptation of the heart in.diabetes: Part II: Potential mechanisms. Circulation Apr. 16, 2002;105(15):1861-70.

Hajri T, Ibrahimi A, Coburn CT, Knapp Jr FF, Kurtz T, Pravenec M, et al. Defective fatty acid uptake in the spontaneously hypertensive rat is a primary determinant of altered glucose metabolism, hyperinsulinemia, and myocardial hypertrophy. J Biol Chem Jun. 29, 2001;276(26):23661-6.

(56) References Cited

OTHER PUBLICATIONS

McGuinness MC, Zhang HP, Smith KD. Evaluation of pharmacological induction of fatty acid beta-oxidation in X-linked adrenoleukodystrophy. Mol Genet Metab Sep.-Oct. 2001;74(1-2):256-63.

Subramanian A, Tamayo P, Mootha VK, Mukherjee S, Ebert BL, Gillette MA, et al. Gene set enrichment analysis: a knowledge-based approach for interpreting genome-wide expression profiles. Proc Natl Acad Sci U S A Oct. 25, 2005;102(43):15545-50.

Benjamini YHY. Controlling the false discovery rate: a practical and powerful approach to multiple testing. J Royal Statistical Soc B 1995;57:289-300.

Takahashi N, Calderone A, Izzo Jr NJ, Maki TM, Marsh JD, Colucci WS. Hypertrophic stimuli induce transforming growth factor-beta 1 expression in rat ventricular myocytes. J.Clin Invest Oct. 1994;94(4):1470-6.

Siwik DA, Chang DL, Colucci WS. Interleukin-1beta and tumor necrosis factoralpha decrease collagen synthesis and increase matrix metalloproteinase activity in cardiac fibroblasts in vitro. Circ Res Jun. 23, 2000;86(12):1259-65.

Marin-Garcia J, Goldenthal MJ. Mitochondrial centrality in heart failure. Heart Fail Rev Jun. 2008;13(2):137-50.

Brower GL, Levick SP, Janicki JS. Inhibition of matrix metalloproteinase activity by ACE inhibitors prevents left ventricular remodeling in a rat model of heart failure. Am J Physiol Heart Circ Physiol Jun. 2007;292(6):H3057-64.

Frey N, Olson EN. Modulating cardiac hypertrophy by manipulating myocardial lipid metabolism? Circulation Mar. 12, 2002;105(10):1152-4.

Taegtmeyer H, Wilson CR, Razeghi P, Sharma S. Metabolic energetics and genetics in the heart. Ann N Y Acad Sci Jun. 2005;1047:208-18.

Finck BN, Kelly DP. Peroxisome proliferator-activated receptor gamma coactivator-1 (PGC-1) regulatory cascade in cardiac physiology and disease. Circulation May 15, 2007;115(19):2540-8.

de Wilde J, Mohren R, van den Berg S, Boekschoten M, Dijk KW, de Groot P, et al. Short-term high fat-feeding results in morphological and metabolic adaptations in the skeletal muscle of C57BL/6 J mice. Physiol Genomics Feb. 19, 2008;32(3):360-9.

Rauchhaus M, Doehner W, Francis DP, Davos C, Kemp M, Liebenthal C, et al. Plasma cytokine parameters and mortality in patients with chronic heart failure. Circulation Dec. 19, 2000;102(25):3060-7.

Sivakumar P, Gupta S, Sarkar S, Sen S. Upregulation of lysyl oxidase and MMPs during cardiac remodeling in human dilated cardiomyopathy. Mol Cell Biochem Jan. 2008;307(1-2):159-67.

Bergman MR, Kao RH, McCune SA, Holycross BJ. Myocardial tumor necrosis factoralpha secretion in hypertensive and heart failure-prone rats. Am J Physiol Aug. 1999;277(2 Pt 2):H543-50.

Chen Y, Park S, Li Y, Missov E, Hou M, Han X, et al. Alterations of gene expression in failing myocardium following left ventricular assist device support. Physiol Genomics Aug. 15, 2003;14(3):251-60.

Jahanyar J, Joyce DL, Southard RE, Loebe M, Noon GP, Koerner MM, et al. Decorinmediated transforming growth factor-beta inhibition ameliorates adverse cardiac remodeling. J Heart Lung Transplant Jan. 2007;26(1):34-40.

Sekiguchi K, Tian Q, Ishiyama M, Burchfield J, Gao F, Mann DL, et al. Inhibition of PPAR-alpha activity in mice with cardiac-restricted expression of tumor necrosis factor: potential role of TGF-beta/Smad3. Am J Physiol Heart Circ Physiol Mar. 2007;292(3):H1443-51.

Wright JM, Zeitlin PL, Cebotaru L, Guggino SE, Guggino WB. Gene expression profile analysis of 4-phenylbutyrate treatment of IB3-1 bronchial epithelial cell line demonstrates a major influence on heat-shock proteins. Physiol Genomics Jan. 15, 2004;16(2):204-11.

Kee HJ, Sohn IS, Nam KI, Park JE, Qian YR, Yin Z, et al. Inhibition of histone deacetylation blocks cardiac hypertrophy induced by angiotensin II infusion and aortic banding. Circulation Jan. 3, 2006;113(1):51-9.

Singh OV, Vij N, Mogayzel Jr PJ, Jozwik C, Pollard HB, Zeitlin PL. Pharmacoproteomics of 4-phenylbutyrate-treated IB3-1 cystic fibrosis bronchial epithelial cells. J Proteome Res Mar. 2006;5(3):562-71.

Bing OH, Fanburg BL, Brooks WW, Matsushita S. The effect of lathyrogen betaamino proprionitrile (BAPN) on the mechanical properties of experimentally hypertrophied rat cardiac muscle. Circ Res Oct. 1978;43(4):632-7.

Cheng XW, Obata K, Kuzuya M, Izawa H, Nakamura K, Asai E, et al. Elastolytic cathepsin induction/activation system exists in myocardium and is upregulated in hypertensive heart failure. Hypertension Nov. 2006;48(5):979-87.

Khairallah RJ, Khairallah M, Gelinas R, Bouchard B, Young ME, Allen BG, et al. Cyclic GMP signaling in cardiomyocytes modulates fatty acid trafficking and prevents triglyceride accumulation. J Mol Cell Cardiol Aug. 2008;45(2):230-9.

Yamauchi S, Takeishi Y, Minamihaba O, Arimoto T, Hirono O, Takahashi H, et al. Angiotensin-converting enzyme inhibition improves cardiac fatty acid metabolism in patients with congestive heart failure. Nucl Med Commun Aug. 2003;24(8):901-6.

Brooks WW, Shen SS, Conrad CH, Goldstein RH, Bing OHL. Transition from compensated hypertrophy to systolic heart failure in the spontaneously hypertensive rat: Structure, function, and transcript analysis. Genomics 95 (2010) 84-92.

Brooks WW, Shen SS, Conrad CH, Goldstein RH, Deng LL, Bing OHL. Transcriptional changes associated with recovery from heart failure in the SHR. Journal of Molecular and Cellular Cardiology 49 (2010) 390-401.

Dyer ES, Paulsen MT, Markwart SM, Goh M, Livant DL and Ljungman M. Phenylbutyrate Inhibits the Invasive Properties of Prostate and Breast Cancer Cell Lines in the Sea Urchin Embryo Basement Membrane Invasion Assay. Int. J. Cancer: (2002) 101, 496-499.

Office Action dated Apr. 24, 2012, in co-pending divisional U.S. Appl. No. 13/137,636, filed Aug. 31, 2011.

\* cited by examiner

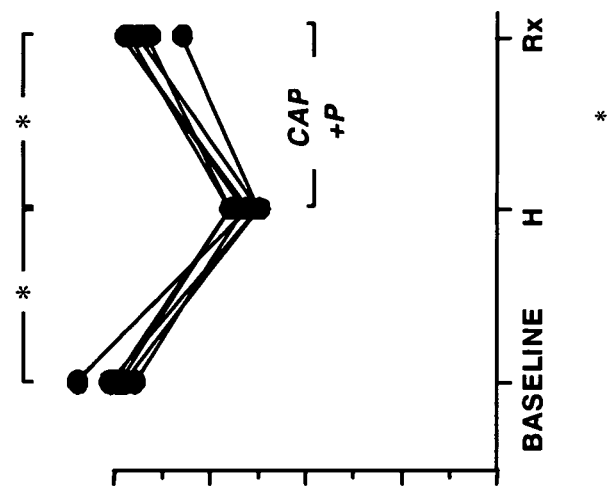
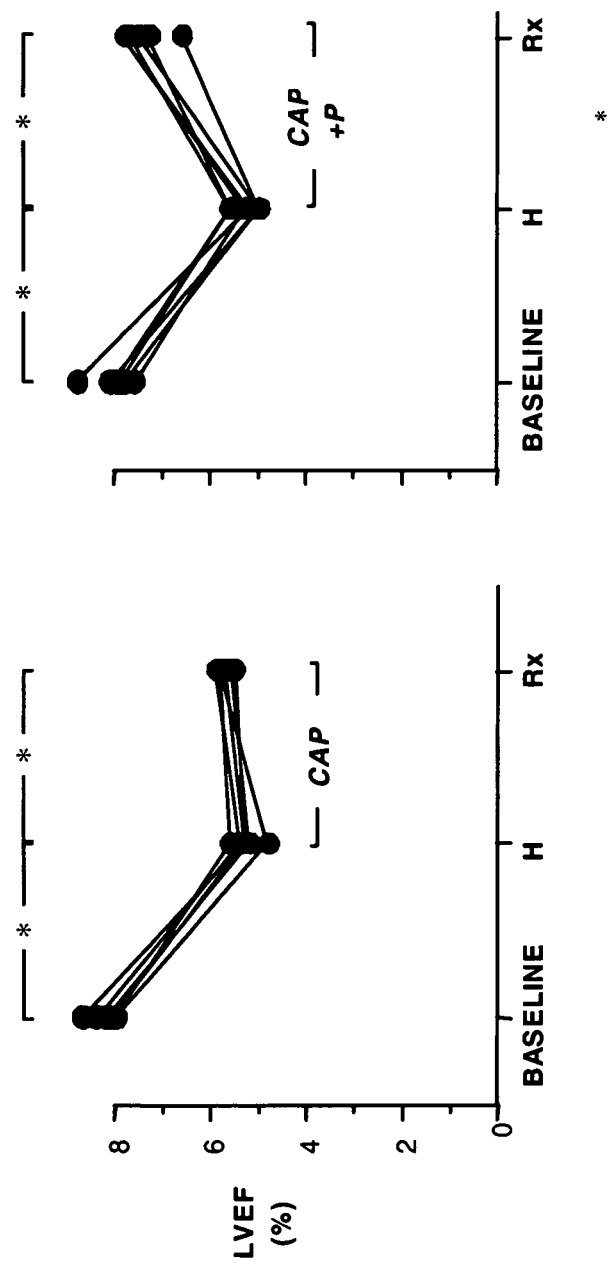
FIG. 2A
FIG. 2B

Proposed schema

Known Drug Actions

Captopril (ACE Inhibitor)

- Inhibits formation of Angiotensin II
- Decreases: Hypertrophy
  Apoptosis
  Vasoconstriction

Phenylbutyrate (HDAC Inhibitor)

- Inhibits deacetylation of chromatin
- Increases transcription

FIG. 10

METHOD AND COMPOSITION FOR TREATING HEART FAILURE

CROSS-REFERENCE TO RELATED APPLICATIONS

The present application claims priority on prior U.S. Provisional Application Ser. No. 60/960,598, filed Oct. 5, 2007, which is hereby incorporated herein in its entirety by reference.

STATEMENT REGARDING FEDERALLY SPONSORED RESEARCH OR DEVELOPMENT

The work leading to the present invention was supported by one or more grants from the U.S. Government, and specifically the VA merit review grant entitled "Restoration of Function in the Failing Heart". The U.S. Government therefore has certain rights in the invention.

FIELD AND BACKGROUND OF THE INVENTION

The present invention is generally directed to cardiac therapy, and more particularly to treating, preventing, or ameliorating heart failure and/or cardiac hypertrophy, and/or dysfunction by reactivating silenced adult cardiac gene expression.

Heart failure is a leading case of death and disability. Hospitalization and long-term care for this condition represent major health care costs items. Among other entities, hypertension is a major factor underlying the development of heart failure.

Neither the cause of hypertension or mechanisms underlying heart failure are fully understood. It is clear, however, that increased neurohormonal activity accompanies heart failure and ameliorating this activity by beta adrenergic antagonists and inhibitors of the rennin-angiotensin aldosterone system improves clinical state. These treatments represent cornerstones in the management of heart failure today.

Although symptomatic improvement in heart failure patients is found with neurohumoral blockade, reversal of the underlying pathophysiology does not take place. Pathological events include adverse remodeling of the myocardium, associated with a modification of gene expression, an increase in left ventricular mass, depression of intrinsic myocardial function.

Conventional treatments for heart failure are designed to stabilize disease progression and are primarily limited to the administration of an angiotensin converting enzyme (ACE) inhibitor, angiotensin receptor blocker, beta adrenergic blocker, or diuretic. For example, a ACE inhibitor, such as captopril, is frequently administered to patients with hypertension and acutely decompensated heart failure. The efficacy of ACE inhibitors, such as captopril, is based on their ability to reduce circulation levels of angiotensin 11, to thereby reduce mean arterial pressure and systemic vascular resistance. This results in decreased workload on the heart in patients with heart failure. This treatment may temporarily reduce clinical symptoms of heart failure, however, does not effectively treat the underlying disease and the long-term outlook for heart failure patients remains poor.

Much of the pathophysiology associated with heart failure may be due, in large part, to abnormal gene transcription that results from aberrant silencing of adult cardiac gene expression and recapitulation of the fetal gene program. Histone acetylase and deacetylaces can play a role in the control of gene expression. A prior patent document (US Patent Application Publication No. 2006/0025333) entitled "Inhibition of histone deacetylases as a treatment for cardiac hypertrophy" provides methods for treatment and prevention of cardiac hypertrophy in patients at risk of developing heart failure by administration of class II histone deacetylases (HDAC) inhibitors, consisting of tricoststin A, trapoxin B, MS 275-27, m-carboxycinnamic acid bis-hydroxamide, depudecin, oxamflatin, apicidin, suberoylanilide hydroxamic acid, Scriptaid, pyroxamide, 2-amino-8oxo-9,10-epoxy-decanoyl, 3-(4-aroyl-1H-pyrrol-2-yl)-N-hydroxy-2--propenamide and FR901228. However, it is noted that this patent document does not include phenylbutyrate. Aside from the actions of HDACs, when DNA is methylated in the promotor region of genes, where transcription is initiated, normal adult genes are inactivated and silenced (Reference 1), which can lead to recapitulation of the fetal gene profile that characterizes the failing heart.

As noted above, angiotensin converting enzyme inhibitors, the primary standard treatment for hypertension and heart failure, are designed to stabilize disease progression. However, myocardial dysfunction involving depressed myocardial contractility and cardiac enlargement due, in large part, to pathologic gene expression remains unresolved. An approach to selectively target cardiac gene transcription to alter gene expression, and thereby restore the adult cardiac profile, reduce ventricular mass and increase contractile function is needed to effectively treat heart failure.

Histone deacetylase inhibitors are substances causing inhibition of the activity of histone deacetylase, resulting in hyperacetylation and leading to chromatin relaxation and wide scale changes of gene expression. Current compounds shown to inhibit the activity of histone deacetylases fall into six structurally diverse classes. Phenylbutyrate (MW 164.21), comprises the short chain fatty acid class and is well-tolerated clinically at drug concentrations, which effect acetylation of histones in vitro. Phenylbutyrate has been used for the treatment of urea cycle disorders in children, sickle cell disease, thalassemia, cancer and more recently for the treatment of cystic fibrosis and ALS disease. However, thus far, phenylbutyrate has not been used for the treatment of heart failure.

OBJECTS AND SUMMARY OF THE INVENTION

The principal object of the present invention is to provide a method and composition for treating a patient and other mammals having heart failure.

Another object of the present invention is to provide a method and composition for reversing the underlying disease process for heart failure or cardiac hypertrophy.

Another object of the present invention is to provide a pharmaceutical composition and method for the treatment of acute and chronic heart failure.

Another object of the present invention is to provide a pharmaceutical composition that targets gene changes of the heart, and method for the treatment of myocardial dysfunction involving reestablishment of normal cardiac gene transcription to induce adult proteins and regress ventricular enlargement due to heart failure.

Another object of the present invention is to provide compositions and methods to treat patients and animals with congestive heart failure by administration of an ACE inhibitor and an effective amount of a combined inhibitor of histone deacetylase and DNA methylation.

Another object of present invention is a combined use of phenylbutyrate, a histone deacetylase inhibitor, together with a angiotensin converting enzyme inhibitor, such as captopril for the treatment of heart failure.

Another object of the present invention is to provide a new treatment for heart failure which accompanies the use of an angiotensin converting enzyme inhibitor, such as captopril (a standard treatment for the management of heart failure) with phenylbutyrate. While use of angiotensin converting enzyme inhibitors alone has been found to improve clinical state, the gene expression changes associated with heart failure are minimally modified. Left ventricular hypertrophy and myocardial contractile state are not improved. Adding phenylbutyrate to angiotensin converting enzyme inhibitor results in reversal of numerous gene expression changes, amelioration of left ventricular hypertrophy and contractile dysfunction. Thus, simultaneous administration of an angiotensin converting enzyme inhibitor to stabilize hemodynamics together with phenylbutyrate to modulate gene expression is demonstrated in the present invention to provide an effective method for the treatment of heart failure.

In summary, the invention employs a therapeutic strategy that utilizes a combination of drugs to modulate the expression of cardiac genes involved in the pathogenesis of heart failure. More specifically, compositions and methods are provided for treating aberrant silencing of adult cardiac gene expression and deactivation of the fetal gene profile associated with heart failure through inhibition of DNA methylation and histone deacetylation in combination with a sulfhydryl-containing angiotensin converting enzyme inhibitor. The method comprises administering to a patient or mammal suffering from heart failure a therapeutically effective amount of sodium phenylbutyrate, an inhibitor of histone deacetylase, which is metabolized in the human body by beta-oxidation to phenylacetate, a hypomethylating agent, in combination with an effective amount of the angiotensin converting enzyme inhibitor captopril. The present invention, therefore, provides method and composition for treating, preventing or ameliorating heart-failure and cardiac hypertrophy and dysfunction by reactivating silenced adult cardiac gene expression.

BRIEF DESCRIPTION OF THE DRAWINGS

The present invention will be more fully understood and further advantages will become apparent when reference is made to the following description of the invention and the accompanying Figures, in which:

The drawings are the result of data obtained from 6 animals per group. Age matched groups are 1) non-failing SHR, 2) SHR with heart failure, 3) failing SHR treated with captopril (2 g/L in the drinking water) for 30 days, and 4) failing SHR treated with phenylbutyrate (6 g/L in the drinking water) and captopril for 30 days.

FIGS. 2A-2B represent serial echocardiographic measurements (n=6 animals per group) of LV ejection fraction (LVEF) from individual SHR obtained before the onset of heart failure (Baseline), at the time of heart failure (HF) and following 30 days of treatment (Rx) with either captopril (CAPT—FIG. 2A) or combined captopril and phenylbutyrate treatment (CAPT+PB—FIG. 2B). Note marked reduction in LVEF with HF. There was marked improvement with combined treatment, as compared to minimal improvement with captopril alone.

FIG. 10 illustrates the primary pharmacological drug actions of captopril and phenylbutyrate.

DETAILED DESCRIPTION OF THE PREFERRED EMBODIMENT(S) OF THE INVENTION

Figures 1A, 1B:
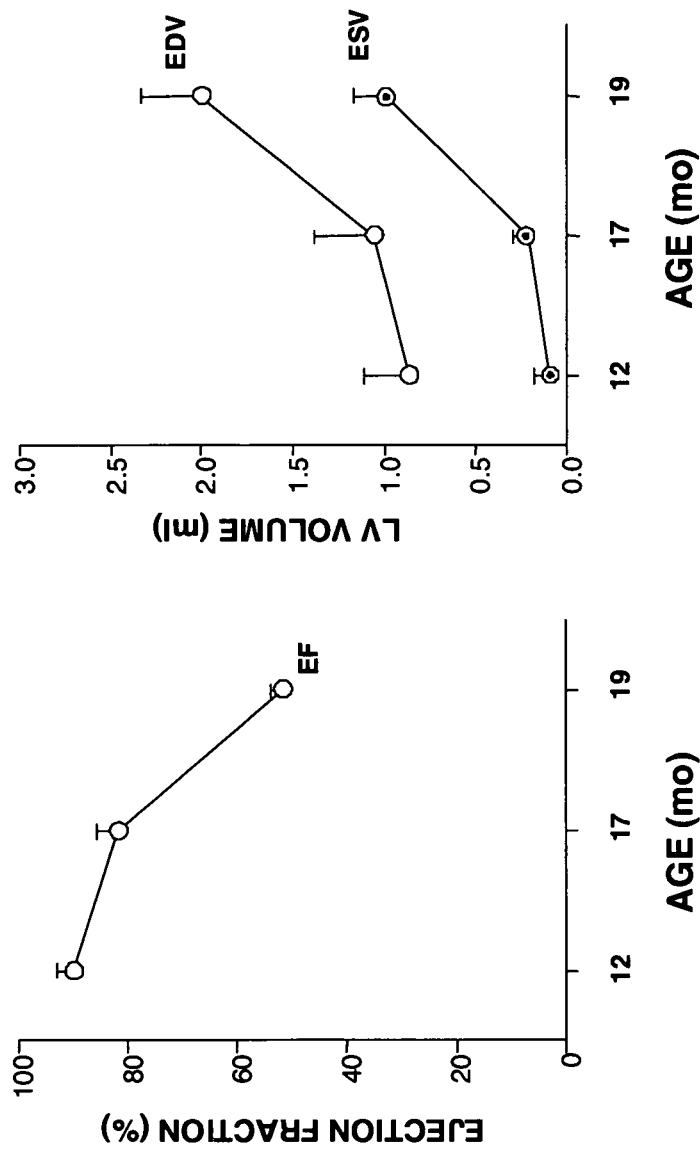
FIGS. 1A-1B illustrate serial echocardiographic measurements in SHR. LV ejection fraction (FIG. 1A) and end-systolic and end-diastolic LV volume (FIG. 1B) of male SHR during the transition to heart failure (12, 17, and 19 months of age). EF, LV ejection fraction (%); ESV, end-systolic volume (ml); EDV, end-diastolic volume (ml). LV function remains compensated until approximately 17 months, and then rapidly declines; mean age at onset of heart failure 19±1 months.
Figure 3:
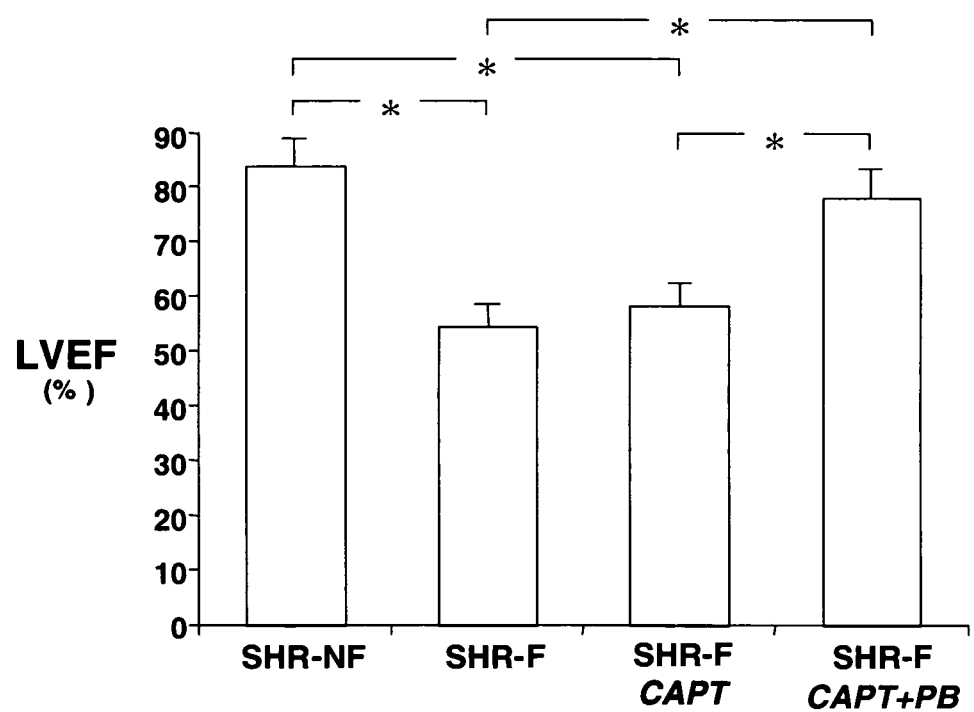
FIG. 3 illustrates LV ejection fraction (LVEF) in non-failing SHR (SHR-NF), SHR with HF (SHR-F) and SHR-F following 30 days of captopril (CAPT) or combined phenylbutyrate and captopril treatment (CAPT+PB). There was no significant change in LVEF with CAPT. In contrast, LVEF with CAPT+PB increased to near control. Data are mean±SD (n=6 per group).

The present invention discloses a composition and method for reestablishing adult cardiac gene transcription through inhibition of histone deacetylases and DNA methylation by the use of phenylbutyrate in combination with a angiotensin converting enzyme inhibitor, such as captopril or a pharmaceutically acceptable salt thereof, for the preparation of a pharmaceutical composition for the treatment of heart failure.

Based on studies in a genetic model of hypertension and heart failure the spontaneously hypertensive rat, a new treatment for heart failure is described, which reverses: 1) changes in cardiac gene expression associated with heart failure, 2) biventricular hypertrophy, and 3) myocardial dysfunction. The mechanism of treatment effect of phenylbutyrate, as an adjunct treatment, with standard angiotensin converting enzyme (ACE) inhibition (e.g. captopril) is suggested to be through its action as a histone deacetylase inhibitor. Phenylbutyrate is a non-specific histone deacetylase inhibitor that is already approved by the Food and Drug Administration to treat ornithine transcarbamylase deficiency.

Phenylbutyrate and its derivatives thereof are disclosed to be useful as adjunct agents for treatment in heart failure. Pharmaceutical formulations and the use of compounds of phenylbutyrate in combination with other agents (e.g. captopril) are also disclosed.

Phenylbutyrate is a natural nontoxic colorless tasteless aromatic fatty acid purified from mammalian urine and plasma, is Food and Drug Administration approved for children with hyperammonemia associated with inborn errors of urea synthesis.

In the course of our experiments, we discovered phenylbutyrate strongly affected cardiac gene expression, cardiac hypertrophy and contractile function of myocardial muscle with heart failure.

Phenylbutyrate is one of six structurally diverse classes of compounds that inhibit the activity of histone deacetylases (HDAC). Phenylbutyrate is of the short chain fatty acid class. Sodium phenylbutyrate is an FDA approved orphan drug (i.e. Buphenyl) for clinical use in urea cycle disorders such as ornithine transcarbamylase deficiency (Reference 2). In humans phenylbutyrate is metabolized by beta-oxidation to phenylacetate which is conjugated with glutamine to phenylacetylglutamine, that is eliminated with the urine. However, phenylacetate also exhibits hypomethylation activity (Reference 3) independent of its effects on nitrogen metabolism. In animals without heart failure oral administration of phenylbutyrate has been shown to inhibit histone deacetylase activity (References 4 and 5) and DNA methylation (Reference 6) at pharmacologic concentrations that results in numerous changes in tissue gene expression in vivo.

Captopril is a sulfhydral-containing analog of proline that competitively inhibits angiotensin converting enzyme, thereby decreasing circulating and tissue levels of angiotensin 11, increasing plasma renin activity and decreasing aldosterone secretion to reduce blood pressure. Captopril is FDA approved as an antihypertensive drug for the treatment of hypertension.

A compound including a phenylbutyrate structure and a pharmaceutically acceptable angiotensin converting enzyme inhibitor (i.e. captopril) are mixed together as a single preparation for oral administration to simultaneously stabilize disease progression and target transcriptional changes of the heart in the treatment of humans and animals with heart failure.

The histone deactylase inhibitor, phenylbutyrate, can be used in the form of a pharmaceutically acceptable salt. As such it may be used so long as it does not adversely affect the desired pharmacological effects of the compound. Examples of pharmaceutically acceptable salts include, alkali metal salts such as sodium salt or a potassium salt, alkaline earth metal salts such as calcium salt or magnesium salt, salts with an organic base such as an ammonium salt, or a salt with no organic base such as triethylamine salt or an ethanolamine salt. Sodium-free glycerol-mono-phenylbutyrate ester could also be used in patients who might be harmed by large sodium load.

The use of a histone deacetylase inhibitor and angiotensin converting enzyme inhibitor or combined agent of the present invention may be administered in the form of soft and hard capsules, tablets, granules, powders, solutions, suspensions or the like. In the case of non-oral administration, they may be administered in the form of injections solution, drip infusion formulations or patches or the like, whereby continued membrane absorption can be maintained in the form of solid, viscous liquid, or suspension. The selection of the method for the delivery of these formulations and the vehicles, disintegrators or suspending agents, can be readily made by those skilled in the art. The use is of a combined agent, including a histone deacetylase inhibitor, such as phenylbutyrate, and a angiotensin converting enzyme inhibitor, such as captopril or pharmaceutically acceptable salts thereof.

As recognized by those skilled in the art, the effective dose would vary depending on route of administration, excipient usage, and the possibility of co-use of phenylbutyrate with other therapeutic treatments, such as the use of angiotensin converting enzyme inhibitors other than captopril, or angiotensin converting enzyme receptor blockers, or beta adrenergic receptor blockers, or diuretics, or other standard heart failure drug treatments. Effective amounts and treatment regimens for any particular subject (e.g., human, dog, horse or cat) will also depend upon a variety of other factors, including the activity of the specific compound employed, age, body weight, general health status, sex diet time of administration, rate of excretion, severity and course of the disease, and the patient's disposition to the disease, but are usually from 1.0 to 30 grams of phenylbutyrate per day irrespective of the manner of administration.

In order that the invention described herein may be more readily understood, the following examples are set forth. It should be understood that these examples are for illustrative purposes only and are not to be construed as limiting this invention in any manner.

EXAMPLE 1

Figure 5A:
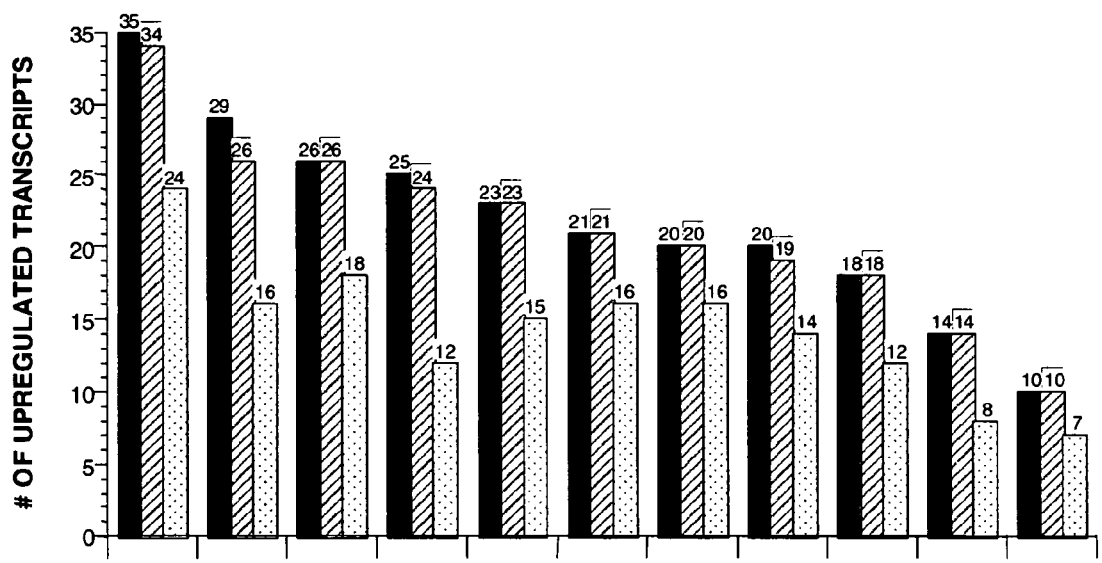
FIG. 5A illustrates identified transcripts whose expression was increased with HF and returned toward non-failing levels with treatment. Transcripts are grouped by functional categories based on Affymetrix gene ontology and biological process annotations. Solid bars: SHR-F, hatched bars: CAPT; stippled bars: CAPT+PB.
Figure 5B:
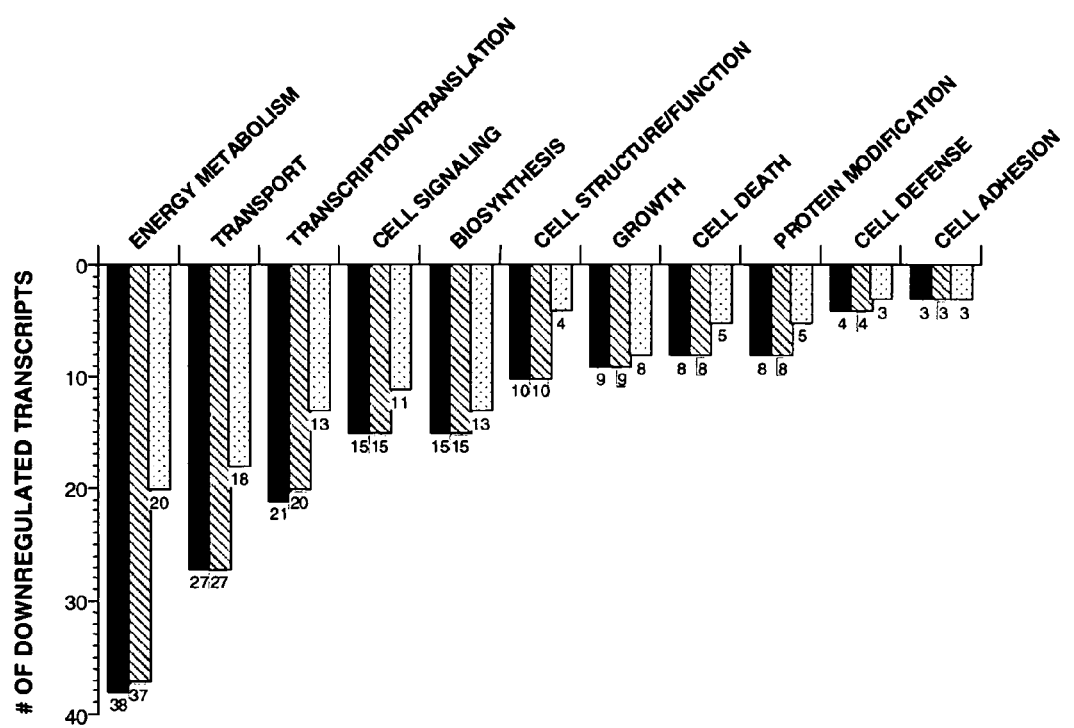
FIG. 5B illustrates identified transcripts whose expression was decreased with HF and returned toward non-failing levels with treatment. Transcripts are grouped by functional categories based on Affymetrix gene ontology and biological process annotations. Solid bars: SHR-F, hatched bars: CAPT; stippled bars: CAPT+PB.
Figures 7A, 7B:
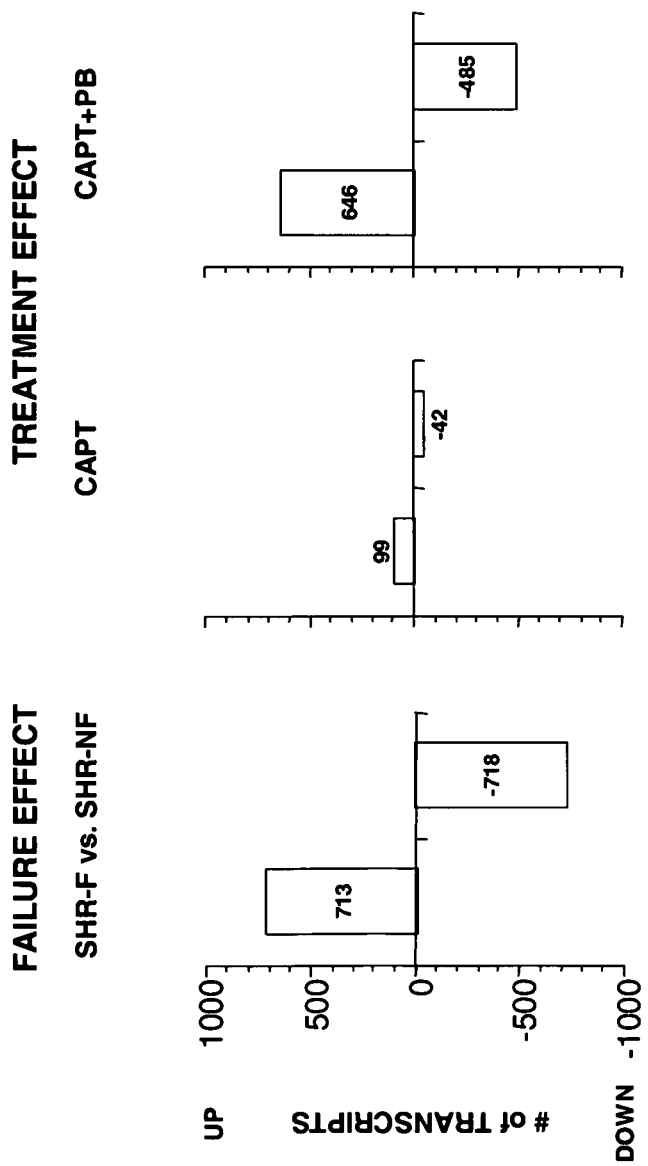
FIG. 7A illustrates failure effect. Total number of transcripts significantly different ($p<0.05$) between LV samples from SHR-F compared to SHR-NF.
FIG. 7B illustrates treatment effect. Total number of transcripts significantly different ($p<0.01$) between SHR-F and SHR-F with CAPT or CAPT+PB.
Figures 8A, 8B:
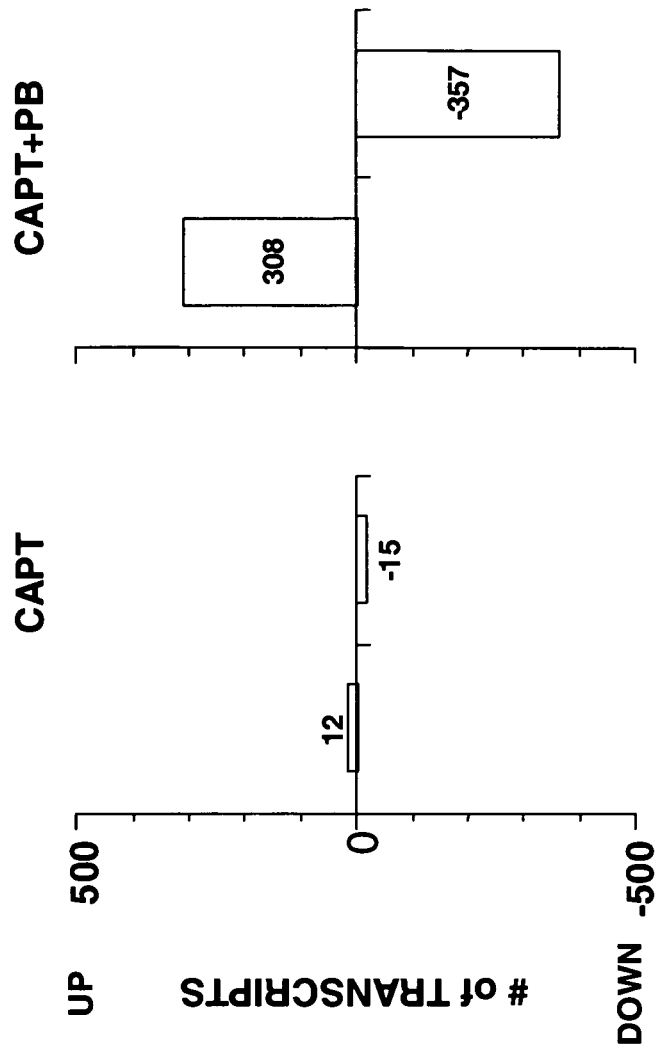
FIG. 8A illustrates failure effect. Total number of transcripts significantly different ($p<0.05$) between LV samples from SHR-F compared to SHR-NF.
FIG. 8B illustrates treatment effect. Total number of transcripts significantly different ($p<0.01$) between SHR-F and SHR-F with CAPT or CAPT+PB.

A Combined Histone Deacetylase Inhibitor and Angiotensin Converting Enzyme Inhibitor Treatment is Effective for Heart Failure Adult male spontaneously hypertensive rats (SHR) rats were purchased as retired breeders from Taconic Inc and boarded in the animal facility at the Boston VA Healthcare system until the time of study (18 to 24 months of age). Each rat was caged alone and allowed free access to chow and water. Animals were monitored several times per week for evidence of tachypnea and labored respiration; when these clinical findings were clearly in evidence, animals were either killed and studied or treated with captopril and/or phenylbutyrate. Groups of animals were treated by adding the angiotensin converting enzyme inhibitor captopril to the drinking water (2 g/L to drinking water) and/or phenylbutyrate to the drinking water (6 g/L to the drinking water; sodium 4-phenylbutyrate (Triple Crown America, Inc.)) when clinical evidence of impaired cardiac function was detected. Treatment was continued for 30 days, the animals closely monitored and then studied. A control group of age-matched, untreated SHR rats was used for comparison. At autopsy, animals were examined for pleural or pericardial effusions, atrial thrombi, and right and left ventricular hypertrophy. The heart was lightly blotted and weight, and individual cardiac chambers were quickly dissected, and chamber weight recorded. Left ventricular tissue samples were rapidly frozen and stored in liquid nitrogen for later mRNA analysis. Subsequently, total RNA was isolated from all left ventricular samples and subjected to individual Affymetrix (230 2.0) array analysis (performed at the Genomics Laboratory of Boston University School of Medicine, Boston Mass.). Six individual animals were included in each experimental group.

mRNA Analysis of Left Ventricular Tissue from SHR with Heart Failure Treated with Phenylbutyrate and Captopril or Without Treatment Statistical analysis identified 1431 genes from the 28,000 probesets surveyed that were significantly different (p<0.05) between non-failing SHR and SHR with heart failure. Of these, 713 genes were up-regulated and 718 were down-regulated. FIGS. 7A-7B provide a visual summary of the quantitative changes in transcripts observed with heart failure (SHR-F) compared to non-failing gene expression (SHR-F vs. SHR-NF) and those effects of treatment (SHR-F+C and SHR-F+CP) relative to un-treated SHR with heart failure. Fewer than 2% of transcripts were significantly modified with captopril treatment (p<0.01). Captopril treatment (alone) reversed expression of 27 identified genes 12 were down-regulated and 15 were up-regulated which were overexpressed and repressed, respectively, with heart failure. FIGS. 8A-8B provide a summary of the number of identified transcripts whose expression was reversed following treatment relative to un-treated SHR with failure. In contrast, phenylbutyrate when combined with captopril treatment reversed expression of more than 47% of heart failure-induced changes in gene expression (p<0.01). The expression of 665 genes were reversed when phenylbutyrate was added to captopril therapy (i.e. 308 were down-regulated and 357 up-regulated that were induced and repressed, respectively, with failure; see FIGS. 8A-8B). Cardiac left ventricular tissue showed a dramatic change in global gene expression, including induction or repression of numerous genes affecting multiple cellular processes, as presented in FIGS. 5A and 5B, which was strongly linked to the improved physiologic state. Analysis of pooled mRNA samples of right ventricular tissue indicate relatively few genes were differentially expressed between LV and RV tissue either with failure or treatment (data not shown). LV and RV are similarly affected by heart failure and amenable to therapeutic treatment effects. Taken together, these findings are consistent with the concept that phenylbutyrate acts as a wide scale inhibitor of transcription to reverse aspects of adverse remodeling and dysfunction associated with heart failure.

EXAMPLE 2

The Ventricular Mass Increases with Heart Failure

Figure 4A:
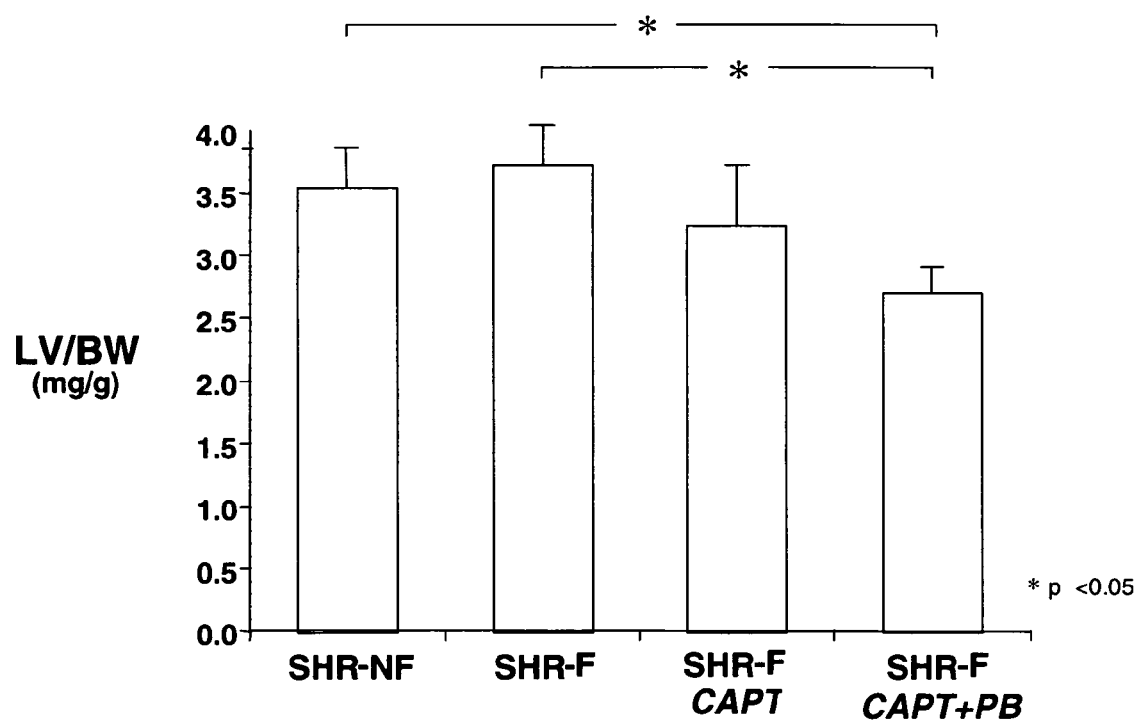
FIG. 4A illustrates LV/BW ratio, an index of LV hypertrophy, in non-failing SHR (SHR-NF), SHR with HF (SHR-F) and SHR-F following 30 days of captopril (CAPT) or combined treatment (CAPT+PB). There was no significant reduction in LV/BW with CAPT. In contrast, LV/BW with CAPT+PB was less as compared to untreated SHR, with or without HF. Data are mean±SD (n=6 per group).
Figure 4B:
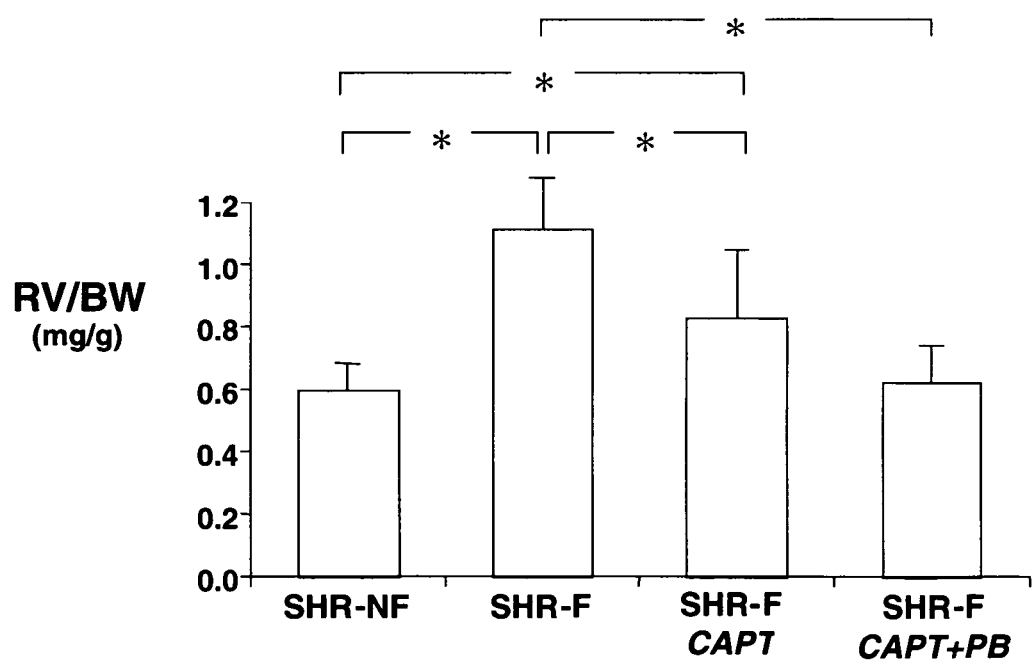
FIG. 4B illustrates RV/BW ratio, an index of RV hypertrophy, in non-failing SHR (SHR-NF), SHR with HF (SHR-F) and SHR-F following 30 days of captopril (CAPT) or combined treatment (CAPT+PB). RV/BW was increased with HF, and decreased with treatment. Data are mean±SD (n=6 per group).

There is an increase in left and, to a greater extent, right ventricular weight with heart failure in SHR rats. See Table 1 and FIGS. 4A and 4B.

Table 1 (below) summarizes body weight, cardiac chamber weight, and ratios with and without treatment. Referring to Table 1, four groups of six SHR/group were examined: non-treated SHR with heart failure (SHR-F), age matched controls without heart failure (SHR-NF), and SHR with heart failure treated with the angiotensin converting enzyme inhibitor captopril (2 g/L in drinking water) (SHR-F+C) or captopril combined with the histone deacetylase inhibitor phenylbutyrate (6 g/L in the drinking water) for 30 days (SHR-F+CP). The results show changes in the pathological tissue weight between the SHR with heart failure (SHR-F) and non-failing SHR groups (SHR-NF), and the group treated with phenylbutyrate, and, to a far lesser extent, the captopril treated group. It was observed that SHR rats with heart failure had enlarged hearts and increased cardiac chamber weights relative to non-failing SHR group and the captopril treated SHR groups. In contrast, the rats treated with phenylbutyrate and captopril had far smaller cardiac chamber weights. There were no significant differences in body weight among the experimental groups. Indices of cardiac hypertrophy (i.e. LV/body weight ratio and RV/body weight ratios) were reduced with phenylbutyrate treatment. Cardiac chamber weight to tibia length data confirmed these findings. See the following Table 1.

TABLE 1

|  | BW (g) | LV wt. (mg) | RV wt. (mg) | LV/body wt. (ratio) | RV/body wt. (ratio) |
|---|---|---|---|---|---|
| SHR-NF | 404 ± 34 | 1.3 ± 0.1 | 0.23 ± 0.04$^+$ | 3.2 ± 0.3$^+$ | 0.57 ± 0.10$^+$ |
| SHR-F | 362 ± 30 | 1.4 ± 0.1 | 0.41 ± 0.05* | 3.9 ± 0.3* | 1.12 ± 0.17* |
| SHR-F + C | 404 ± 28 | 1.3 ± 0.1 | 0.34 ± 0.07*$^+$ | 3.3 ± 0.3$^+$ | 0.86 ± 0.20$^{+*}$ |
| SHR-F + CP | 403 ± 24 | 1.0 ± 0.1*$^{+\#}$ | 0.25 ± 0.06$^+$ | 2.5 ± 0.2*$^{+\#}$ | 0.62 ± 0.12$^+$ |

BW = body weight;
HT wt. = total heart weight;
LV wt. = left ventricular weight;
RV wt. = right ventricular weight;
LV/body wt. = left ventricular to body weight ratio;
RV/body wt. = ratio of right ventricular to body weight ratio.
Values are means ± SD.
*$p < 0.05$ vs. SHR-NF;
$^+p < 0.01$ vs. SHR-F;
$^\#p < 0.01$ vs. SHR-F + C Phenylbutyrate as an adjunct treatment for heart failure mediates regression of adverse cardiac remodeling.

EXAMPLE 3

Effect of Phenylbutyrate and Captopril Treatment on Myocardial Muscle Function of SHR with Heart Failure At the time of sacrifice, left ventricular papillary muscles were dissected free and mounted in an isolated muscle bath containing oxygenated physiologic solution for assessment of mechanical function. Muscle mechanics were measured under computer control of force or length of the preparation. Force and length data were sampled at a rate of 1 kHz and stored on disk for later analysis.

Table 2 (below) summarizes the changes in left ventricular papillary muscle mechanical function obtained from SHR with heart failure (SHR-F), age-matched non-failing SHR (SHR-NF), and SHR with heart failure treated at the time of failure with captopril (SHR-F+C; 2 g/l in the drinking water) or captopril and phenylbutyrate (SHR-F+CP; 6 g/l in the drinking water). Treatment was continued for 30 days and then the animals studied.

TABLE 2

| | AT (g/mm$^2$) | +dT/dt (g/mm$^2$/s) | RT$_{1/2}$ (ms) | V$_{1.0}$ (muscle length/s) | Kwm (stiffness) |
|---|---|---|---|---|---|
| SHR-NF | 4.3 ± 0.3 | 43.1 ± 8.6 | 188 ± 14 | 1.4 ± 0.4 | 53.2 ± 4.3 |
| SHR-F | 2.5 ± 0.7* | 22.2 ± 6.8 | 144 ± 14* | 0.7 ± 0.2* | 73.5 ± 14.1* |
| SHR-F + C | 2.7 ± 0.4* | 28.4 ± 8.0 | 148 ± 25* | 0.9 ± 0.2* | 73.9 ± 4.2* |
| SHR-F + CP | 5.3 ± 1.8$^{+\#}$ | 56.3 ± 9.0$^{+\#}$ | 184 ± 21 | 1.6 ± 0.2$^{+\#}$ | 64.6 ± 10.6 |

AT = active tension;
+dT/dt = rate of tension development;
RT$_{1/2}$ = relaxation time index;
V$_{1.0}$ = shortening velocity;
Kwm = whole muscle stiffness.
Values are means ± SD.
*p < 0.05 vs. SHR-NF;
$^+$p < 0.01 vs. SHR-F;
$^\#$p < 0.01 vs SHR-F + C Captopril treatment of SHR with heart failure did not restore contractile function or reduce passive muscle stiffness. In contrast, when phenylbutyrate was added to captopril treatment contractile dysfunction was reversed.

In conclusion, phenylbutyrate is a active compound for the treatment of heart failure when used in conjunction with captopril. Combined compound treatment ameliorates changes in cardiac gene expression, chronic enlargement of ventricular mass and depression of cardiac contractile muscle function associated with heart failure. The present invention also relates to a method for the treatment of humans or animals afflicted with either acute or chronic heart failure, comprising administering to the subject an effective amount of a histone deacetylases inhibitor combined with a angiotensin converting enzyme inhibitor in particular phenylbutyrate and captopril, respectively, or pharmaceutically acceptable salts thereof and optionally a suitable excipient.

All of the features disclosed in this specification may be combined in any combination. Each feature disclosed in this specification may be replaced by an alternative feature serving the same, equivalent, or similar purpose. Thus, unless expressly stated otherwise, each feature disclosed is only an example of a generic series of equivalent or similar features.

From the above description, one skilled in the art can easily ascertain the essential characteristics of the present invention, and without departing from the spirit and scope thereof, can make various changes and modifications of the invention to adapt it to various usages and conditions. For example, compounds structurally and functionally analogous to phenylbutyrate described above can also be used in combination with other angiotensin converting enzyme inhibitor other than captopril to practice the present invention. Thus, other embodiments are also within the claims.

Discussion

Figure 6A:
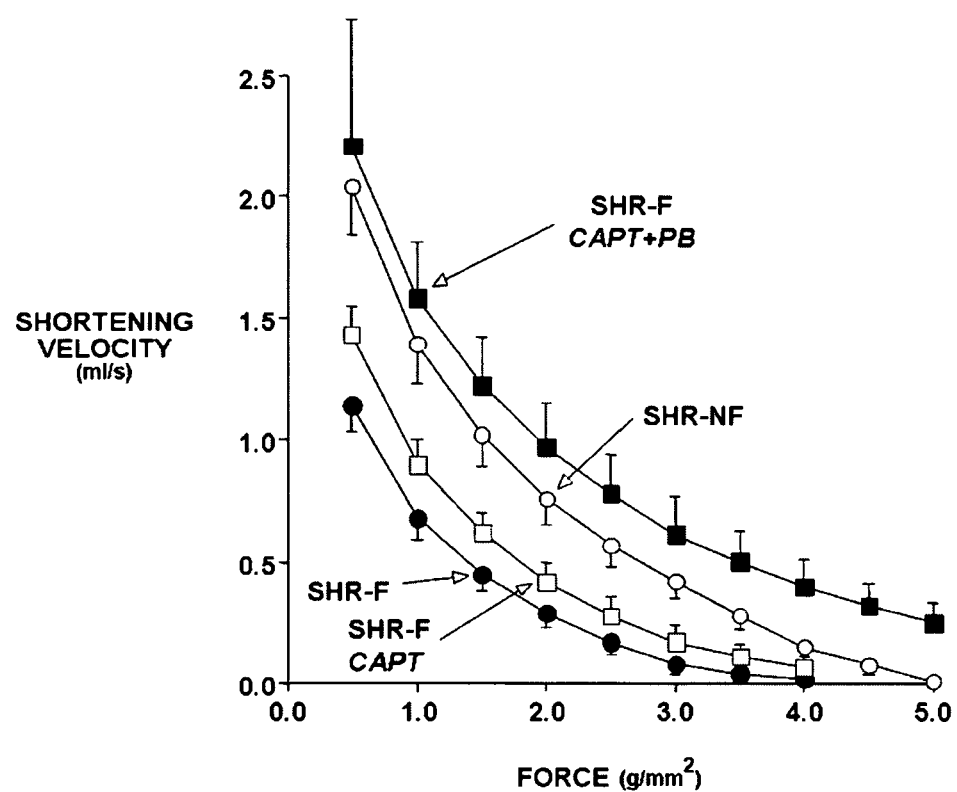
FIG. 6A illustrates quick release force-velocity (F-V) relationships from LV papillary muscles. F-V relationships were significantly depressed ($p<0.01$) in SHR-F in comparison to SHR-NF. F-V relationships were not significantly increased with CAPT, but were significantly greater with CPT+PB. Data are mean±SD (n=6 per group).
Figure 6B:
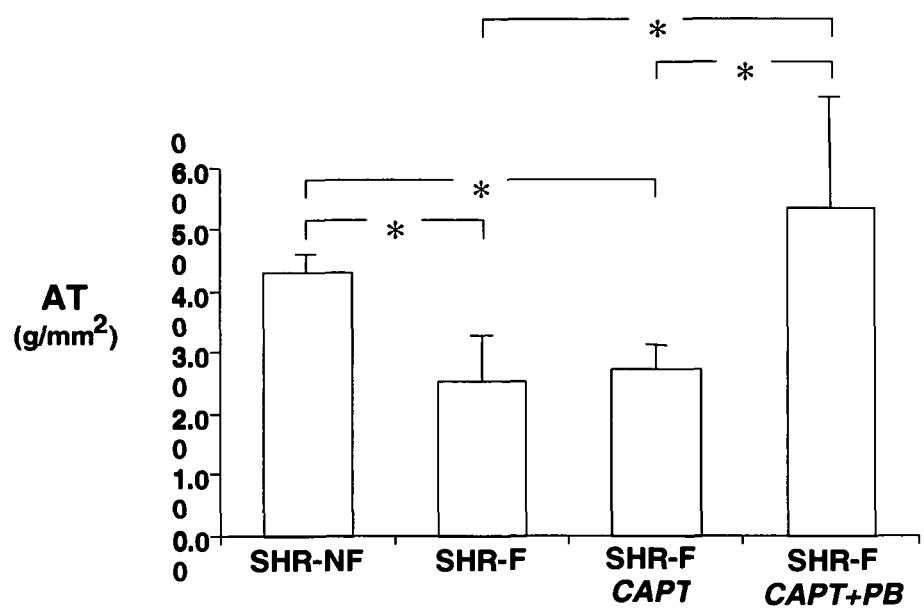
FIG. 6B illustrates active tension (AT) of LV papillary muscles. AT Active tension was significantly depressed ($p<0.01$) in SHR-F in comparison to SHR-NF. CAPT did not improve AT compared to SHR-F. AT was significantly greater with CAPT+PB as compared to SHR-F and CAPT. Data are mean±SD (n=6 per group).
Figure 9:
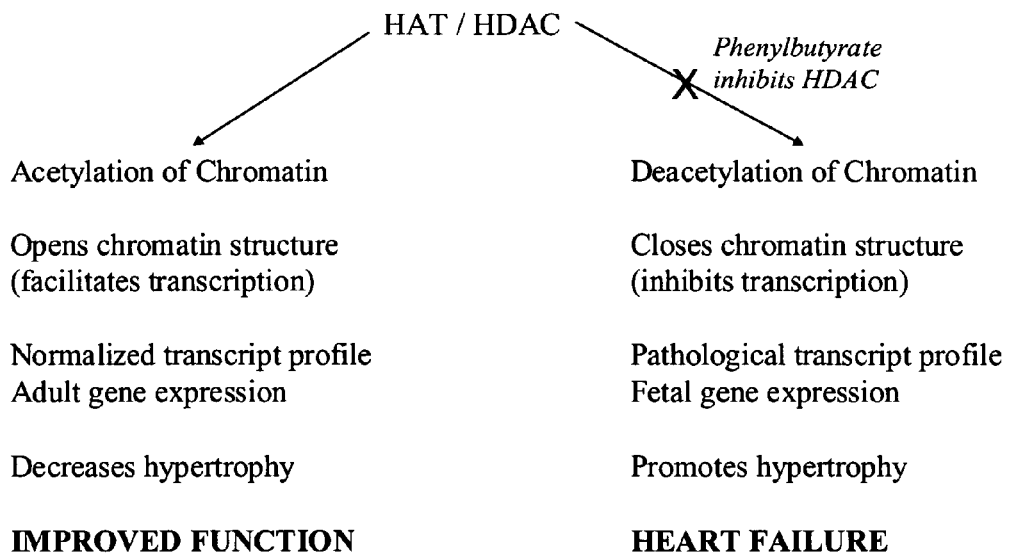
FIG. 9 illustrates the proposed mechanism by which phenylbutyrate is likely to modulate cardiac gene transcription.

We have shown (Reference 7) that treatment of spontaneously hypertensive rats with heart failure of a combined mixture phenylbutyrate and captopril together administered in the drinking water for 30 days, but not captopril alone, can reverse expression of 655 heart failure associated genes (determined by Affymetrix gene chip array analysis and results confirmed by real time PCR of selected transcripts) which was associated with reduced right and left ventricular (LV) hypertrophy (see FIGS. 4A and 4B), improved LV ejection fraction in vivo (determined by echocardiogram; see FIGS. 1A-1B and 2A-2B), LV papillary muscle function (see FIGS. 6A and 6B) and beta-adrenergic responsiveness in vitro (data not shown). This study suggests that reestablishing gene transcription through phenylbutyrate's inhibition of histone deacetylase (HDAC) and DNA methylation represents a promising adjunct treatment when combined with ACE inhibition that can reverse many of the adverse pathophysiologic changes found in the failing heart. The findings that phenylbutyrate improves gene transcription and clinical symptoms in a rat model of heart failure, indicates that this combined treatment strategy may be considered for therapeutic targeting of cardiac gene transcription for the treatment of patients with heart failure. It is likely that epigenetic mechanisms may underlie many pathophysiological changes with heart failure. The histone deacetylase inhibitory actions of phenylbutyrate appears to be an effective adjunctive treatment to modulate transcription and cause changes in expression of many heart failure associated genes. FIG. 9 describes the proposed mechanism by which phenylbutyrate is likely to modulate cardiac gene transcription. Phenylbutyrate by inhibiting histone deacetylase (HDAC) promotes gene transcription and thereby improves cardiac function (see FIG. 10).

Treatment Reverses Intrinsic Myocardial Dysfunction and Genotypic Changes Associated with Heart Failure Current treatment for heart failure stabilizes hemodynamics but improvement in intrinsic cardiac muscle function has not been demonstrated. We studied isolated papillary muscle function in the spontaneously hypertensive rat (SHR) which develops heart failure (HF) between 18-24 month of age. Four groups of SHR each consisting of six animals were examined: non-treated SHR with HF (SHR-F), age matched controls without HF (SHR-NF), and SHR with HF that were treated with the ACE inhibitor captopril (2 g/L in drinking water) (SHR-F+C) or captopril combined with the histone deacetylase inhibitor phenylbutyrate (6 g/L in drinking water) for 30 days (SHR-F+CP). FIG. 8 shows the primary pharmacological drug actions of captopril and phenylbutyrate. Following treatment, hearts were isolated and contractile function of LV papillary muscles studied. LV weight and histology were assessed. RNA was isolated from 24 LV samples and subjected to individual Affymetrix (230 2.0) array analysis. Table 3 (below) summarizes the physiological, histological and gene expression findings from this study. Quantitative histological examination of myocardial fibrosis revealed no differences in fibrosis among treatment groups. Statistical analysis identified 1431 genes from the 28,000 genes surveyed that were significantly different (p<0.05) between SHR-F and SHR-NF: 713 genes were upregulated and 718 were downregulated in SHR-F as compared to SHR-NF (see FIGS. 7A-7B). Captopril was found to significantly reverse the change in expression of 141 genes (9.8%) while phenylbutyrate+captopril reversed 1131 (79.0%) (both p<0.01 vs. SHR-F; see FIGS. 7A-7B). Table 4 lists the eight identified genes whose expression was significantly altered with heart failure and subsequently reversed following captopril treatment. In contrast to captopril treatment alone, Table 5a and 5b lists the many identified gene changes that were up-regulated and down-regulated, respectively, with combined phenylbutyrate and captopril treatment. Although combined treatment induced changes in gene expression involving many cell processes, many changes were closely associated with suppression of death associated processes (i.e apoptosis and proteolysis related gene expression). Thus, captopril stabilizes hemodynamics with heart failure and provides a window to treat underlying cardiac dysfunction, but did not improve intrinsic contractile function. The addition of phenylbutyrate to ACE inhibitor resulted in reversal of changes in transcripts, hypertrophy and myocardial dysfunction associated with heart failure.

TABLE 3

|  | LV/Body Weight (ratio) | AT (g/mm$^2$) | $V_{0.1}$ (muscle lengths/s) | Fibrosis (%) | Gene Expression (number) |
| --- | --- | --- | --- | --- | --- |
| SHR-NF | 3.6 ± 0.4 | 4.3 ± 0.3 | 1.4 ± 0.4 | 12.5 ± 3.5 |  |
| SHR-F | 3.8 ± 0.3 | 2.5 ± 0.7* | 0.7 ± 0.2* | 21.9 ± 3.6* | 713↑* 718↓* |
| SHR-F + C | 3.3 ± 0.4 | 2.7 ± 0.4* | 0.9 ± 0.2* | 22.8 ± 3.1* | 42↓† 99↑† |
| SHR-F + CP | 2.7 ± 0.2*,† | 5.3 ± 1.8†,§ | 1.6 ± 0.2†,§ | 18.4 ± 4.0* | 485↓†,§ 646↑†,§ |

AT = active tension;
$V_{0.1}$ = shortening velocity mean ± SD.
*p < 0.05 vs. SHR-NF.
†p < 0.01 vs. SHR-F.
§p < 0.01 vs. SHR-F + C.

TABLE 4

List of Identified Gene Changes with Heart Failure, Reversed by Captopril Treatment (p < 0.01), Ranked by Fold Change.

| Identifier | Gene Description | Fold change F/NF | Function |
| --- | --- | --- | --- |
| NM_017272 | aldehyde dehydrogenase family 1, | 2.34 | B |
| NM_031145 | calcium and integrin binding 1 | 1.27 | CA |
| NM_138823 | protein phosphatase 1, regulatory (inhibitor) subunit 2 | 1.24 | CS |
| BG663093 | sequestosome 1 | 1.23 | TT |
| NM_017038 | protein phosphatase 1A, magnesium dependent, alpha isoform | 1.23 | CS |
| NM_017039 | protein phosphatase 2a, catalytic subunit, alpha isoform | 1.11 | CS |
| BI282044 | acetyl-CoA transporter | 0.77 | EM |
| NM_012555 | v-ets erythroblastosis virus E26 oncogene homolog 1 | 0.67 | TT |

Expression is given as a fold difference of expression present in the SHR-F transcriptional profile relative to that of SHR-NF.
B, Biosynthesis,
CA, cell adhesion or binding activity;
CS, cell signaling/communication;
EM, energy metabolism;
TT, transcription/translation regulatory activity.

TABLE 5a

Transcripts Up-Regulated with Heart Failure (p < 0.05) and Significantly Down-Regulated with Combined Treatment (p < 0.01). Up-Regulated Transcripts Ranked by Fold Change

| Identifier | Description | Fold change F/NF | Function |
| --- | --- | --- | --- |
| Up-Regulated with failure < with Rx | | | |
| BF289368 | lipopolysaccharide binding protein | 6.11 | CD |
| NM_053611 | nuclear protein 1 | 3.11 | TT |

TABLE 5a-continued

Transcripts Up-Regulated with Heart Failure (p < 0.05) and Significantly Down-Regulated with Combined Treatment (p < 0.01). Up-Regulated Transcripts Ranked by Fold Change

| Identifier | Description | Fold change F/NF | Function |
|---|---|---|---|
| NM_053326 | enigma homolog | 2.96 | CS |
| NM_031832 | lectin, galactose binding, soluble 3 | 2.9 | CA |
| BF419200 | CCAAT/enhancer binding protein (C/EBP), delta | 2.73 | TT |
| NM_012620 | serine (or cysteine) proteinase inhibitor, clade E, member 1 | 2.77 | CS |
| AF245040 | Dickkopf homolog 3 | 2.68 | CS |
| NM_017080 | hydroxysteroid 11-beta dehydrogenase 1 | 2.65 | B |
| D63648 | phospholipase B | 2.55 | EM |
| AI716896 | secreted frizzled-related protein 1 | 2.54 | D |
| NM_017320 | cathepsin S | 2.50 | D |
| BI304009 | lysyl oxidase | 2.42 | PM |
| NM_017272 | aldehyde dehydrogenase family 1, Subfamily A4 | 2.34 | B |
| NM_021663 | nucleobindin 2 | 2.23 | CA |
| BI298314 | von Willebrand factor | 2.20 | CD |
| NM_020104 | fast myosin alkali light chain | 2.19 | S |
| NM_134401 | cartilage acidic protein 1 | 2.19 | CA |
| NM_012905 | aortic preferentially expressed gene 1 | 2.19 | TT |
| AF290212 | calcium channel, voltage-dependent, T type, alpha 1G subunit | 2.11 | T |
| NM_017237 | ubiquitin carboxy-terminal hydrolase L1 | 2.07 | B |
| NM_053629 | follistatin-like 3 | 1.97 | CS |
| AB032395 | decay accelarating factor 1 | 1.90 | CD |
| AB049572 | sphingosine kinase 1 | 1.8 | D |
| NM_012846 | fibroblast growth factor 1 | 1.84 | G |
| AJ277077 | damage-specific DNA binding protein 1 | 1.84 | TT |
| NM_031514 | Janus kinase 2 | 1.82 | CS |
| NM_031684 | solute carrier family 29 (nucleosid transporters), member 1 | 1.79 | T |
| AW253722 | RAB13, member RAS oncogene family | 1.73 | CS |
| BI296610 | glutamine synthetase 1 | 1.68 | B |
| NM_031740 | UDP-Gal:betaGlcNAc beta 1,4-galactosyltransferase, polypeptide 6 | 1.68 | B |
| NM_053555 | vesicle-associated membrane protein 5 | 1.67 | S |
| BI297004 | PX domain containing serine/threonine | 1.64 | CS |
| L38615 | glutathione synthetase | 1.64 | B |
| AF051335 | reticulon 4 | 1.59 | CD |
| BI284461 | v-maf musculoaponeurotic fibrosarcoma oncogene family, protein K | 1.59 | TT |
| AI176519 | immediate early response 3 | 1.58 | G |
| D88666 | phosphatidylserine-specific phospholipase A1 | 1.58 | M |
| BI303655 | ATPase, Na+/K+ transporting, beta 3 polypeptide | 1.56 | T |
| NM_053857 | eukaryotic translation initiation factor 4E binding protein 1 | 1.53 | TT |
| J02612 | UDP glycosyltransferase 1 family, polypeptide A1 /// UDP (Ugt1a6 /// Ugt1a7 /// Ugt1a4 /// Ugt1a8 /// Ugt1a2 /// Ugt1a1) glycosyltransferase 1 family, polypeptide A6 /// UDP glycosyltransferase 1 family, polypeptide A7 /// UDP glycosyltransferase 1 family, polypeptide A8 /// UDP glycosyltransferase 1 family polypeptide A2 /// UDP glycosyltransferase 1 family polypeptide A4 /// UDP glycosyltransferase 1 family polypeptide A11 /// UDP glycosyltransferase 1 family, polypeptide A5 | 1.52 | B * |
| NM_012636 | parathyroid hormone-like peptide | 1.51 | CS |
| NM_017334 | cAMP responsive element modulator | 1.50 | TT |
| AI176595 | cathepsin L | 1.50 | D |
| AI576297 | programmed cell death 4 | 1.49 | D |
| NM_031576 | P450 (cytochrome) oxidoreductase | 1.47 | EM |
| BI278802 | prion protein | 1.46 | CD |
| NM_017022 | integrin beta 1 | 1.45 | CA |
| U75920 | microtubule-associated protein 1b | 1.43 | S |
| NM_053653 | vascular endothelial growth factor C | 1.42 | G |
| L12407 | dopamine beta hydroxylase | 1.41 | B |
| BI303379 | tumor necrosis factor receptor superfamily, member 12a | 1.41 | CD |
| BM391807 | acyl-Coenzyme A dehydrogenase family, member 9 | 1.38 | EM |
| NM_031646 | receptor (calcitonin) activity modifying protein 2 | 1.38 | CS |
| BE112590 | discoidin domain receptor family, member 1 | 1.37 | CS |

TABLE 5a-continued

Transcripts Up-Regulated with Heart Failure (p < 0.05) and Significantly Down-Regulated with Combined Treatment (p < 0.01). Up-Regulated Transcripts Ranked by Fold Change

| Identifier | Description | Fold change F/NF | Function |
|---|---|---|---|
| NM_134449 | protein kinase C, delta binding protein | 1.31 | CG |
| BE097791 | meningioma expressed antigen 5 (hyaluronidase) | 1.31 | B |
| NM_031823 | Wolfram syndrome 1 | 1.30 | B |
| BM383722 | NCK-associated protein 1 | 1.29 | D |
| NM_012734 | hexokinase 1 | 1.28 | EM |
| NM_019124 | rabaptin 5 | 1.28 | D |
| NM_031145 | calcium and integrin binding 1 | 1.27 | CA |
| AW527957 | Bcl2-like 2 | 1.25 | D |
| BG671677 | amyloid beta (A4) precursor protein. | 1.25 | CD |
| AI008441 | phosphogluconate dehydrogenase | 1.25 | EM |
| NM_138823 | protein phosphatase 1, regulatory (inhibitory) subunit 2 | 1.24 | CS |
| BG663093 | sequestosome 1 | 1.23 | TT |
| AI237597 | heat shock protein 1, alpha | 1.23 | PM |
| BI282866 | lamin A | 1.23 | S |
| NM_017038 | protein phosphatase 1A, magnesium dependent, alpha isoform | 1.23 | CS |
| NM_017039 | protein phosphatase 2a, catalytic subunit, beta isoform | 1.22 | TT |
| M83143 | sialyltransferase 1 | 1.22 | PM |
| BG668463 | nitrilase 1 | 1.21 | B |
| NM_053739 | beclin 1 (coiled-coil, myosin-like BCL2-interacting protein) | 1.20 | CD |
| NM_022531 | desmin | 1.18 | S |
| NM_053522 | ras homolog gene family, member Q | 1.18 | CS |
| M86443 | hypoxanthine guanine phosphoribosyl transferase | 1.17 | B |
| BF283010 | syntaxin 12 | 1.17 | T |
| NM_053290 | phosphoglycerate mutase 1 | 1.16 | EM |
| NM_031785 | ATPase, H+ transporting, lysosomal (vacuolar proton pump), subunit 1 | 1.16 | T |
| BE329377 | Jun D proto-oncogene | 1.15 | TT |
| AA850867 | gamma sarcoglycan | 1.13 | S |
| M62763 | sterol carrier protein 2 | 1.2 | B |
| NM_017039 | protein phosphatase 2a, catalytic subunit, alpha isoform | 1.11 | TT |
| NM_017039 | protein phosphatase 2a, catalytic subunit, alpha isoform | 1.11 | TT |
| NM_022523 | CD151 antigen | 1.07 | CA |

CA, cell adhesion or binding activity;
CD, cell defense (i.e. immunity/oxidative stress);
CS, cell signaling/communication;
D, death associated;
E, enzyme activity;
G, cell growth/maintenance;
M metabolism;
PM, protein or structural modifier;
S, cell structure (i.e. ECM) or function (i.e. contraction);
T, transport;
TT, transcription/translation regulatory activity.

TABLE 5b

Transcripts Down-Regulated with Heart Failure (p < 0.05) and Significantly Up-Regulated with Combined Treatment (p < 0.01). Down-Regulated Transcripts Ranked by Fold Change

| Identifier | Description | Fold change F/NF | Function |
|---|---|---|---|
| | Down-Regulated with failure > with Rx | | |
| AI535411 | myosin, heavy polypeptide 7, cardiac muscle, beta | 0.18 | S |
| AI103845 | UDP-N-acetyl-alpha-D-galactosamine:polypeptide N-acetylgalactosaminyltransferase 13 | 0.28 | PM |

TABLE 5b-continued

Transcripts Down-Regulated with Heart Failure (p < 0.05) and Significantly Up-Regulated with Combined Treatment (p < 0.01). Down-Regulated Transcripts Ranked by Fold Change

| Identifier | Description | Fold change F/NF | Function |
|---|---|---|---|
| AF385402 | potassium channel, subfamily K, member 2 | 0.33 | T |
| M74449 | potassium voltage-gated channel, shaker related subfamily, member 2 | 0.34 | T |
| AF134409 | RASD family, member 2 | 0.35 | CS |
| NM_031730 | potassium voltage gated channel, Shai-related family, member 2 | 0.37 | T |
| J02997 | dipeptidylpeptidase 4 | 0.42 | D |
| NM_022604 | endothelial cell-specific molecule 1 | 0.46 | G |
| NM_019174 | carbonic anhydrase 4 | 0.48 | B |
| BE098261 | solute carrier family 25 (mitochondrial oxodicarboxylate carrier) | 0.50 | T |
| NM_033352 | ATP-binding cassette, sub-family D(ALD) member 2 | 0.51 | EM |
| NM_017239 | myosin, heavy polypeptide 6 | 0.52 | S |
| AA799574 | L-3-hydroxyacyl-Coenzyme A dehydrogenase, short chain | 0.52 | EM |
| X95189 | acyl-CoenzymeA oxidase 2, branched chain | 0.52 | EM |
| AI411446 | pyruvate dehydrogenase phosphatase isoenzyme 2 | 0.53 | EM |
| NM_012506 | ATPase Na+/K+ transporting, alpha 3 polypeptide | 0.53 | EM |
| BE113154 | FK506 binding protein 4 | 0.56 | PM |
| AA79 421 | protein kinase C, epsilon | 0.58 | CS |
| BE113289 | peroxisome proliferator-activated receptor gamma coactivator 1 beta | 0.59 | TT |
| NM_031715 | phosphofructokinase, muscle | 0.66 | EM |
| BG378763 | glycerol-3-phosphate dehydrogenase 2 | 0.65 | EM |
| NM_017328 | phosphoglycerate mutase 2 | 0.61 | EM |
| AI411979 | carnitine acetyltransferase | 0.61 | EM |
| NM_012930 | carnitine palmitoyltransferase 2 | 0.67 | EM |
| D88891 | brain acyl-CoA hydrolase | 0.63 | EM |
| BI276974 | valyl-tRNA synthetase 2-like | 0.64 | TT |
| BE111733 | hormone-regulated proliferation-associated 20 kDa protein | 0.65 | D |
| NM_133606 | enoyl-Coenzyme A hydratase/3-hydroxyacyl Coenzyme A dehydrogenase | 0.65 | EM |
| NM_022936 | epoxide hydrolase 2, cytoplasmic | 0.65 | B |
| NM_019156 | vitronectin | 0.66 | CD |
| BF555973 | triadin | 0.66 | S |
| NM_022400 | branched chain aminotransferase 2, mitochondrial | 0.67 | EM |
| AA945624 | NAD(P)H dehydrogenase, quinone 2 | 0.67 | EM |
| NM_012555 | v-ets erythroblastosis virus E26 oncogene homolog 1 | 0.68 | TT |
| NM_012793 | guanidinoacetate methyltransferase | 0.68 | EM |
| AA900057 | PDZ protein Mrt 1 | 0.69 | CS |
| BE113377 | potassium inwardly-rectifying channel, subfamily J, member 11 | 0.70 | TT |
| AI411530 | aminoacylase 1 | 0.70 | D |
| AI235510 | B-cell receptor-associated protein 37 | 0.70 | TT |
| M29853 | cytochrome P450, family 4, subfamily b | 0.74 | EM |
| BM389548 | guanine nucleotide binding protein (G protein), gamma 5 subunit | 0.74 | CS |
| AI177031 | ER transmembrane protein Dri 42 | 0.75 | S |
| NM_031326 | transcription factor A, mitochondrial | 0.77 | TT |
| BI282044 | acetyl-CoA transporter | 0.78 | EM |
| NM_053722 | CLIP associating protein 2 | 0.78 | TT |
| BI296061 | nuclear transcription factor Y-gamma | 0.78 | TT |
| BI289129 | tyrosine kinase receptor 1 | 0.78 | S |
| NM_053483 | karyopherin (importin) alpha 2 | 0.78 | T |
| (Tpm1) | tropomyosin 1, alpha | 0.79 | S |
| U91449 | potassium inwardly-rectifying channel, subfamily J, member 3 | 0.81 | T |
| AA892297 | histone deacetylase 2 | 0.83 | TT |
| NM_031616 | zinc finger 265 | 0.88 | TT |
| NM_012904 | Annexin A1 | 0.89 | EM |
| AA859652 | solute carrier family 16, (monocarboxylic acid transport)membrane 7 | 0.90 | T |
| NM_022385 | ADP-ribosylation factor-1 | 0.92 | T |

CA, cell adhesion or binding activity;
CD, cell defense (i.e. immunity/oxidative stress);
CS, cell signaling/communication;
D, death associated;,
E, enzyme activity;
G, cell growth/maintenance;
M metabolism;
PM, protein or structural modifier;
S, cell structure (i.e. ECM) or function (i.e. contraction);
T, transport;
TT, transcription/translation regulatory activity.

The preliminary findings which have been presented in abstract (Reference 7) form and soon to be submitted for scientific publication describe methods designed to administer a compound mixture including sodium phenylbutyrate and captopril dissolved in the drinking water of animals in need of treatment for heart failure. However, solid dosage forms for oral administration including capsules, tablets, pills, touches, lozenges, powders and granules, containing the active ingredients or intravenous administration may be required to provide maximum therapeutic effectiveness to humans in need of treatment for heart failure. Furthermore, sodium salts are contraindicated in patients with heart failure, it is likely therefore that a compound of these active ingredients including an ester, rather than the sodium salt may be more clinically efficacious.

The description in this application is specifically directed to phenylbutyrate in combination with an angiotensin converting enzyme inhibitor, such as captopril, in the treatment of heart failure and cardiac hypertrophy, as non-limiting examples and is not intended to limit the scope of the invention.

While this invention has been described as having preferred sequences, ranges, steps, materials, structures, features, and/or designs, it is understood that it is capable of further modifications, uses and/or adaptations of the invention following in general the principle of the invention, and including such departures from the present disclosure as those come within the known or customary practice in the art to which the invention pertains, and as may be applied to the central features hereinbefore set forth, and fall within the scope of the invention and of the limits of the appended claims.

REFERENCES

The following references, and those cited in the disclosure herein, are hereby incorporated herein in their entirety by reference.

1. Baylin S B, DNA methylation and gene silencing in cancer. Nature.com/clinicalpractices/oncology. 2005; (suppl 1) 2:S4-10.
2. Maestri N E, Brusilow S W, Clissold D B. Et al., Long-term treatment of girls with ornithine transcarbamylase deficiency. N Engl J Med 1996; 335:855-859.

3. Samid D, Shack S, Myers C E. Selective growth arrest and phenotypic reversion of prostate cancer cells in vitro by non-toxic pharmacological concentrations of phenylacetate. J Clin Invest 1993; 91:2288-2295.
4. Kang H-L, Benzer S, Min K-T, Life extension in *Drosophila* by feeding a drug. Proc Natl Acad Sci USA 2002; 99:838-843.
5. Rishikof D C, Ricupero D A, Liu H, Goldstein R H. Phenylbutyrate decreases type I collagen production in human lung fibroblasts. J Cell Biochem 2004; 91:740-748.
6. Gardian G, Browne S E. Choi D-K, et al., Neuroprotective effects of phenylbutyrate in the N171-82Q transgenic mouse model of Huntington's disease. J Biol Chem. 2005: 280:556-563.
7. Brooks W W, Conrad C H, Marsilio E, Robinson K G, Bing O H L. Treatment reverses myocardial dysfunction and genotypic changes associated with heart failure. J Cardiac Failure 2006; 12:S12. (Abstract #039-August, 2006).
8. Brooks W W, Conrad C H, Marsilio E, Robinson K G, Bing O H L. Reversal of myocardial dysfunction and gene expression changes In the failing heart with histone deacetylase and angiotensin converting enzyme inhibitors. (Abstract submitted to American Heart Association for Circulation on May 30, 2007).
9. Brooks W W, Bing O H L, Robinson K G, Slawsky M T, Chaletsky D M, Conrad C H, Effect of angiotensin-converting enzyme inhibition on myocardial fibrosis and function in hypertrophied and failing myocardium from the spontaneously hypertensive rat. Circulation 1997; 96: 4002-4010.
10. Brooks W W, Bing O H L, Conrad C H, O'Neil L, Crow M T, Lakatta E G, Dostal D E, Baker K M, Boluyt M O, Captopril modifies gene expression in hypertrophied and failing hearts of aged spontaneously hypertensive rats. Hypertension 1997; 30: 1362-1368.
11. Jin H, Yang R, Awad T A, Wang F, Li W, Williams S P, Ogasawara A, Shimada B, Williams M, Feo G, Paoni N F, Effects of early angiotensin converting enzyme inhibition on cardiac gene expression after acute myocardial infarction. Circulation 2001; 103:736-742).
12. U.S. Patent Application Publication No. 2006/0025333, entitled "Inhibition of Histone Deacetylase As A Treatment For Cardiac Hypertrophy."

What is claimed is:

1. A composition for treating or preventing heart failure, comprising:
   a) a histone deacetylase (HDAC) inhibitor or a pharmaceutically acceptable salt or ester thereof; and
   b) an angiotensin converting enzyme (ACE) inhibitor, angiotensin receptor blocker, beta adrenergic receptor blocker, or a pharmaceutically acceptable salt or ester thereof.
2. The composition of claim 1, wherein:
   a) the HDAC inhibitor comprises phenylbutyrate.
3. The composition of claim 2, wherein:
   a) the ACE inhibitor comprises captopril.
4. The composition of claim 1, wherein:
   a) the composition comprises a capsule, tablet, pill, granules, powder, solution, suspension, or patch.
5. The composition of claim 1, wherein:
   a) the pharmaceutically acceptable salt comprises at least one member selected from the group consisting of alkali metal salt, alkaline earth metal salt, organic base salt, and a salt without organic base, and a combination thereof.
6. The composition of claim 1, wherein:
   a) the pharmaceutically acceptable salt comprises at least one member selected from the group consisting of sodium salt, potassium salt, calcium salt, magnesium salt, ammonium salt, triethylamine salt, ethanolamine salt, and a combination thereof.
7. The composition of claim 1, wherein:
   a) the pharmaceutically acceptable ester comprises sodium-free glycerol-mono-phenylbutyrate.
8. A method of treating or preventing heart failure, comprising:
   administering to a subject in need thereof a therapeutically effective amount of a composition including a histone deacetylase (HDAC) inhibitor or a pharmaceutically acceptable salt or ester thereof, and an angiotensin converting enzyme (ACE) inhibitor, angiotensin receptor blocker, beta adrenergic receptor blocker, or a pharmaceutically acceptable salt or ester thereof.
9. The method of treating or preventing heart failure of claim 8, wherein:
   the HDAC inhibitor comprises phenylbutyrate.
10. The method of treating or preventing heart failure of claim 9, wherein:
    the ACE inhibitor comprises captopril.
11. The method of treating or preventing heart failure of claim 8, wherein:
    the composition is administered orally or non-orally.
12. The method of treating or preventing heart failure of claim 8, wherein:
    an oral dose of the HDAC inhibitor or a pharmaceutically acceptable salt or ester thereof comprises about 1 to 30 grams per day with the ACE inhibitor about 0.001 to 1.0 gram per day.
13. The method of treating or preventing heart failure of claim 8, wherein:
    the composition comprises an injection solution, drip infusion formulation, or a patch.
14. The method of treating or preventing heart failure of claim 8, wherein:
    the subject may exhibit one or more symptoms of heart failure, cardiac hypertrophy, and myocardial dysfunction.
15. A method of reversing cardiac gene expression changes associated with heart failure, comprising:
    administering to a subject in need thereof a therapeutically effective amount of a composition including a histone deacetylase (HDAC) inhibitor or a pharmaceutically acceptable salt or ester thereof, and an angiotensin converting enzyme (ACE) inhibitor, angiotensin receptor blocker, beta adrenergic receptor blocker, or a pharmaceutically acceptable salt or ester thereof.
16. A method of reducing or preventing left ventricular hypertrophy, comprising:
    administering to a subject in need thereof a therapeutically effective amount of a composition including a histone deacetylase (HDAC) inhibitor or a pharmaceutically acceptable salt or ester thereof, and an angiotensin converting enzyme (ACE) inhibitor, angiotensin receptor blocker, beta adrenergic receptor blocker, or a pharmaceutically acceptable salt or ester thereof.
17. A method of reversing myocardial dysfunction, comprising:
    administering to a subject in need thereof a therapeutically effective amount of a composition including a histone deacetylase (HDAC) inhibitor or a pharmaceutically acceptable salt or ester thereof, and an angiotensin converting enzyme (ACE) inhibitor, angiotensin receptor blocker, beta adrenergic receptor blocker, or a pharmaceutically acceptable salt or ester thereof.

* * * * *